United States Patent
Andreasen

(10) Patent No.: US 9,439,969 B2
(45) Date of Patent: Sep. 13, 2016

(54) STABLE IRON OLIGOSACCHARIDE COMPOUND

(71) Applicant: Pharmacosmos Holding A/S, Holbæk (DK)

(72) Inventor: Hans Andreasen, Holbæk (DK)

(73) Assignee: Pharmacosmos Holding A/S, Holbaek (DK)

(*) Notice: Subject to any disclaimer, the term of this patent is extended or adjusted under 35 U.S.C. 154(b) by 4 days.

(21) Appl. No.: 14/307,957

(22) Filed: Jun. 18, 2014

(65) Prior Publication Data

US 2014/0303364 A1   Oct. 9, 2014

Related U.S. Application Data

(62) Division of application No. 13/138,669, filed as application No. PCT/DK2009/050069 on Mar. 25, 2009, now Pat. No. 8,815,301.

(51) Int. Cl.
| | |
|---|---|
| C08B 37/02 | (2006.01) |
| A61K 47/26 | (2006.01) |
| C07H 3/06 | (2006.01) |

(52) U.S. Cl.
CPC .............. *A61K 47/26* (2013.01); *C07H 3/06* (2013.01); *C08B 37/0021* (2013.01)

(58) Field of Classification Search
None
See application file for complete search history.

(56) References Cited

U.S. PATENT DOCUMENTS

| | | | |
|---|---|---|---|
| 3,100,202 A | 8/1963 | Muller et al. | |
| 4,518,581 A * | 5/1985 | Miyake | A23K 1/1643 131/274 |
| 4,749,695 A | 6/1988 | Schwengers | |
| 4,927,756 A | 5/1990 | Schwengers | |
| 6,291,440 B1 | 9/2001 | Andreasen et al. | |
| 6,977,249 B1 | 12/2005 | Andreasen et al. | |
| 2003/0083310 A1 | 5/2003 | Andreasen et al. | |
| 2003/0191090 A1 | 10/2003 | Andreasen et al. | |
| 2006/0205691 A1 | 9/2006 | Geisser et al. | |
| 2007/0161600 A1 | 7/2007 | Helenek et al. | |
| 2008/0214496 A1 | 9/2008 | Tanner-Baumgartner et al. | |
| 2010/0266644 A1 | 10/2010 | Helenek et al. | |
| 2010/0305063 A1 | 12/2010 | Reim et al. | |
| 2013/0230565 A1 | 9/2013 | Helenek et al. | |
| 2014/0099381 A1 | 4/2014 | Helenek et al. | |

FOREIGN PATENT DOCUMENTS

| | | |
|---|---|---|
| CA | 623411 A | 7/1961 |
| CA | 623412 A | 7/1961 |
| CA | 2493806 A1 | 5/2004 |
| CA | 2617510 A1 | 3/2007 |
| CA | 2682587 Y | 12/2008 |
| GB | 1076219 A | 7/1967 |
| WO | WO-9711711 A1 | 4/1997 |
| WO | WO-9948533 A1 | 9/1999 |
| WO | WO-0030657 A1 | 6/2000 |
| WO | WO-03087164 A1 | 10/2003 |
| WO | WO-2004037865 A1 | 5/2004 |
| WO | WO-2006084782 A1 | 8/2006 |
| WO | WO-2006111802 A1 | 10/2006 |
| WO | WO-2007023154 A2 | 3/2007 |
| WO | WO-2008145586 A1 | 12/2008 |

OTHER PUBLICATIONS

International Search Report dated Oct. 12, 2009.
Dextran 1 entry European Pharmacopoeia (2004) 5th Edition, published by Council of Europe, Strasbourg, pp. 1408-1409.

* cited by examiner

*Primary Examiner* — Leigh C Maier
(74) *Attorney, Agent, or Firm* — Harness, Dickey & Pierce, P.L.C.

(57) ABSTRACT

The invention relates to an iron oligosaccharide compound with improved stability comprising a hydrogenated oligosaccharide in stable association with ferric oxyhydroxide, the content of dimer saccharide in said hydrogenated oligosaccharide being 2.9% by weight or less, based on the total weight of the hydrogenated oligosaccharide. In further aspects is provided a process for preparing said compound as well as the use of said compound for preparation of a composition for treatment of iron deficiency anaemia.

2 Claims, 1 Drawing Sheet

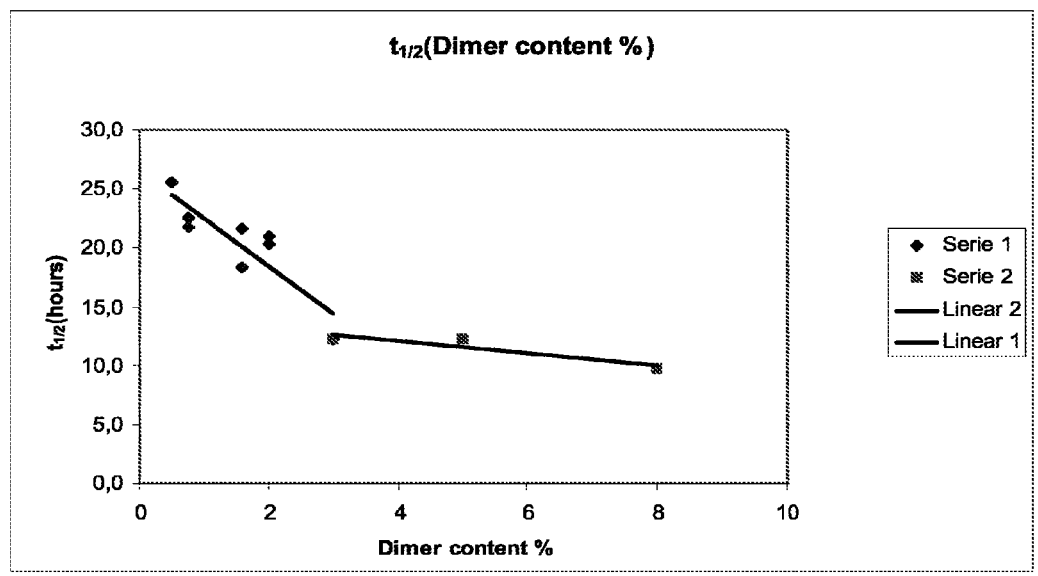

STABLE IRON OLIGOSACCHARIDE COMPOUND

CROSS-REFERENCE TO RELATED APPLICATIONS

The present application is a divisional under 35 U.S.C. §121 of U.S. application Ser. No. 13/138,669, filed Sep. 16, 2011, which is a National Phase Application under 35 U.S.C. §371 of PCT/DK2009/050069, filed Mar. 25, 2009, the entire contents of each of which are incorporated herein by reference.

The present invention relates in a first aspect to an iron oligosaccharide compound with improved stability. In a second aspect, the invention relates to a process for preparing the iron oligosaccharide compound according to the first aspect of the invention. Further, in a third aspect the invention relates to the use of said compound for preparation of a composition for treatment of iron deficiency anaemia.

Due to its widespread occurrence, iron-deficiency anaemia remains a global health issue of major concern. In humans and domestic animals alike it is one of the most frequently observed pathological conditions.

Although iron-deficiency anaemia can often be prevented or cured by oral administration of iron-containing preparations, it is in many cases preferred to use parenterally administrable iron preparations to avoid variations in bioavailability of oral administrations and to ensure effective administration.

Therefore, iron-containing preparations for parenteral use, i.e. subcutaneous, intramuscular or intravenous administration, have for many years been at the disposal of the veterinary or human medical practitioner.

Although various iron-containing substances have been used or suggested as components in parenterally injectable preparations against iron-deficiency anaemia, the most common preparations accepted today are such which comprise a combined product of ferric oxyhydroxide (or ferric hydroxide) in association with a saccharide, notably dextran or dextrin. Dextran is a polymeric carbohydrate produced by the microorganism *Leuconostoc mesenteroides*, while dextrin is a depolymerisation product of starch.

Additional iron preparations for the treatment of iron deficiency anaemia are known, such as iron-sucrose and iron-gluconate compounds. These compounds bind iron less tightly, resulting in a higher concentration of free $Fe^{3+}$ ions, which increases the toxicity of the iron compounds when administered parenterally and may lead to disturbance of digestion when administered orally.

An iron-containing preparation for parenteral injection should obviously satisfy several requirements including ready availability of the iron for haemoglobin synthesis, absence of local or general side-effects and stability on storage enabling a satisfactory shelf-life at ambient temperature.

In some cases, it is desirable to administer an iron preparation orally because this is most convenient for the recipients. A frequent disadvantage encountered after administration of iron preparations orally is impaired digestion. Good iron preparations should provide iron to the body in the gastro-intestinal tract in a controlled way in order to provide sufficient iron to be assimilated through the intestinal epithelium and should not have an adverse influence on the digestion as such.

Iron saccharide preparations for treatment of anaemia have been marketed for decades, and many variations in the manufacturing process and in the selection of starting materials have been suggested with a view to improving the stability of such preparations and to decrease the severity of side-effects encountered at their administration.

Results obtained in investigations, tests and practical experience indicate that the above-mentioned problems are related to the molecular weight distribution of the saccharides employed.

It is generally recognized that high molecular dextrans involve a greater risk of anaphylactic reactions than do low molecular weight dextrans, but is has also been found that the presence of carbohydrates of low molecular weight such as monosaccharides, resulting from an initial step of hydrolysis, may create difficulties as well. When reacted with iron by precipitating ferric hydroxide in a solution of a saccharide with an ample molecular weight distribution, the low molecular weight carbohydrates combine with iron to form complex or association compounds of their own. The latter compounds are less stable than the desired iron oligosaccharide compound of moderate molecular weight, causing precipitation of iron hydroxide or oxyhydroxide and/or gel-forming reactions possibly resulting in a complete solidification of the solution within days or months.

In view of the importance of the issue, considerable attention has been directed to the development of iron oligosaccharide compounds, wherein the oligosaccharide component presents an appropriate molecular weight distribution.

GB 1,076,219 discloses a method for the manufacture of a complex containing iron, low molecular weight dextrin or dextran and sorbitol for the prophylaxis or treatment of iron deficiency anaemia.

U.S. Pat. No. 4,927,756 describes a procedure for the manufacture of an iron dextran compound wherein the molecular weight of the dextrans is in the range of 2000-4000.

WO 1999/48533 discloses iron dextrans consisting of dextrans having a weight average molecular weight of 700 to 1400 and number average molecular weight of 400 to 1400 Daltons in stable association with ferric oxyhydroxide. The disclosed iron dextran complexes give rise to a reduced number of incidences of anaphylactic side effects.

WO 2003/087164 discloses iron dextrin compounds consisting of dextrins of a weight average molecular weight of 3,000 Daltons or less and a number average molecular weight of 400 Daltons or more in stable association with ferric oxyhydroxide. Said compounds show a low degree of toxicity.

In the light of the known methods and compounds mentioned in the above, however, there is still a need for further improving the stability of iron oligosaccharide compounds useable for the preparation of compositions for the treatment or prophylaxis of iron deficiency anaemia, so that they may be stored for an extended period at ambient temperature with no significant deterioration of their most important properties.

It is therefore an object of the present invention to provide an iron oligosaccharide compound with enhanced stability suitable for entering into compositions for the treatment or prophylaxis of iron deficiency anaemia. The compound should still fulfil the usual criteria within the art, which are: 1) high availability of iron for adsorption in the intestine without causing digestion problems when administered orally; 2) provision of iron in a form that is readily adsorbed in the intestine; 3) high availability of iron without risk of toxicity caused by high local concentration of $Fe^{3+}$ when administered parenterally; 4) minimum risk of anaphylactic reaction; 5) high iron content, and 6) ability to form solutions comprising a high amount of iron, which solutions fulfil the basal requirements for pharmaceutical compositions, i.e. being amenable to sterilization, preferably by autoclaving, and which are also stable during storage for a long period at ambient temperatures.

To meet this object, an iron oligosaccharide compound is provided according to the first aspect of the invention, which compound comprises a hydrogenated oligosaccharide in stable association with ferric oxyhydroxide, the hydrogenated oligosaccharide having a weight average molecular weight (Mw) of less than 3,000 Daltons, preferably approximately 1,000 Daltons, the content of dimer saccharide in said hydrogenated oligosaccharide being 2.9% by weight or less, based on the total weight of the hydrogenated oligosaccharide.

By way of example, the starting material for manufacturing of the hydrogenated oligosaccharide used in accordance with the invention may be Dextran 1, which satisfies the European Pharmacopoeia, entry 01/2009:1506. This starting material has according to the European Pharmacopoeia the following specifications: weight average molecular weight (Mw): 850 to 1150 Daltons, fraction with one or two saccharide (i.e. dimer) units: less than 15%, and fraction with more than 9 saccharide units: less than 20% by weight. Usually, the amount of dimer saccharide in Dextran 1 is around 8% by weight. By removing the smaller molecules by, e.g. membrane filtration, the desired amount of dimer saccharide of 2.9% by weight or less is obtained.

In the present context and in the following, the terms "weight average molecular weight" and "number average molecular weight" should be taken as the respective molecular weights of the oligosaccharide at the time where formation of complexes takes place, based on all oligosaccharide molecules from the monomer and upwards.

It has surprisingly been found that the amount of dimer in the oligosaccharide entering into stable association with iron(III)oxyhydroxide is a key factor with regard to the stability of the final compound, and that the effect is exerted in a highly non-linear manner. Usually, iron(III)-oxyhydroxid is the sole component used in the iron saccharide composition according to the invention. However, for certain applications, such as contrast agents having magnetic capabilities, it is desired to use a mixture of iron(II)-oxid and iron(III)-oxyhydroxid. The iron oligosaccharide compound of the invention includes compounds prepared from such mixture.

According to the invention, to present a satisfactory stability, the content of dimer must be brought down to or below 2.9% by weight. Thus, by controlling the amount of dimer in the oligosaccharide before reacting with iron, a stable iron oligosaccharide compound is provided in an effective and cost-efficient way. In the case of dextran or dextrin, which are both glucose polymers comprising α 1,6-bonds as well as α 1,4-bonds, the dimers in question are isomaltose (two glucose monomers joined by an α 1,6-bond) and maltose (two glucose monomers joined by an α 1,4-bond).

Preferably, the content of monomer saccharide in said hydrogenated oligosaccharide is 0.5% by weight or less, based on the total weight of the hydrogenated oligosaccharide. This serves to minimize the risk of toxic effects due to the release of free ferric ions from compounds of monomer and iron, especially when present in preparations for parenteral administration. In said preparations, an elevated concentration of free monomer saccharide, such as glucose, may also be undesirable per se.

According to one embodiment of the invention, the employed hydrogenated oligosaccharide is hydrogenated dextran having a weight average molecular weight (Mw) between 500 and 3000 Daltons, a number average molecular weight (Mn) above 500 Daltons, wherein 90% by weight of said dextran has molecular weights less than 3500 Daltons, and the Mw of the 10% by weight fraction of the dextran having the highest molecular weights is below 4500 Daltons. Preferably, the dextran has been subjected to membrane processes having a cut-off value of between 340 and 800 Daltons. In this way it is ensured that incidents of non-desired side-effects are minimized.

In an alternative embodiment, the hydrogenated oligosaccharide is hydrogenated dextrin having a number average molecular weight (Mn) higher than or equal to 500 Daltons, wherein the 10% fraction of said hydrogenated dextrin having the highest molecular weight has a weight average molecular weight (Mw) of less than 4500 Daltons, and 90% of the dextrins have a molecular weight of less than 3500 Daltons. Said dextrin has low toxicity and an appropriate viscosity that allows easy and reliable handling of solutions of the dextrin.

Suitably, the iron oligosaccharide compound according to the invention has an apparent molecular weight ($M_P$) of 120 to 180 kD. Preferably, the an apparent molecular weight ($M_P$) is between 130 and 160 kD.

It is implied that the apparent molecular weight is measured on an autoclaved aqueous solution prepared by dissolving in 1,000 ml water 400 g powder of hydrogenated oligosaccharide in stable solution with ferric oxyhydroxide, the amount of iron (Fe) of the powder being 25% by weight. Solutions comprising the compounds of the invention prepared by another method or in another concentration may result in an apparent molecular weight, which deviates from the present method.

The apparent molecular weight is measured using size exclusion chromatography. The columns are based on silica particles containing polar diol groups. The calibration is made using dextran and iron dextran as standards and 0.1% sodium azid as eluent.

The amount of iron in the iron oligosaccharide compound of the invention may vary in accordance to the intended use of the final composition. Generally, the amount of iron in the iron oligosaccharide compound is 50% by weight or less. Suitably, the amount of iron oligosaccharide is above 10% by weight.

In one embodiment, the content of dimer in the hydrogenated oligosaccharide is 2.5% by weight or less, alternatively 2.3% by weight or less.

Without wishing to be bound by any specific theory, it is assumed that the dimer in small amounts coordinates to the colloidal particle containing the complex between oligosaccharide and FeOOH. When the content of dimer exceeds 2.9%, the dimer apparently acts as "dissolver" of the colloidal particle, rendering the compound of oligosaccharide and FeOOH unstable and able to gelatinize over time.

In one embodiment of the invention, the iron oligosaccharide compound is sole or partial constituent of a dry powder that preferably has an iron content of 10-50% by weight. Alternatively, the iron oligosaccharide compound may be dissolved or dispersed in an aqueous liquid, preferably yielding an iron content in the resulting solution or dispersion of 1-30% w/v. When used as injection liquids, liquids comprising high amounts of iron offers the advantage that a smaller amount of the liquid needs to be injected in the subject being treated, which obviously is an advantage for the subject being treated as well for the person performing the treatment.

According to a further aspect of the invention, a composition is provided, said composition comprising a pharmacologically effective amount of a compound according to the first aspect of the invention, as well as at least one pharmaceutically acceptable carrier. The composition may be adopted for parenteral, oral or any other form of administration.

A pharmaceutical composition comprising an iron oligosaccharide compound according to the invention may be prepared using procedures that are well known by the skilled person. Examples of compositions for oral use are tablets, capsules, syrups, pastes and mixtures.

Pharmaceutical compositions comprising an iron oligosaccharide compound according to the invention may be formulated with additional nutritional or pharmaceutical agents, such as vitamins, preferably water-soluble vitamins, micronutrients such as trace metals, e.g. cobalt, copper, zinc or selenium, bacteriostatic agents, or antibiotics such as tylosin. Vitamins insoluble in water may even be emulsified into an aqueous solution comprising the iron oligosaccharide compound according to the invention by use of a suitable emulsifier.

According to yet an aspect of the invention, a process for preparing an iron oligosaccharide compound is provided, which process comprises the steps of:

(a) hydrolysing a polysaccharide so as to reduce its molecular weight,
(b) hydrogenating the resulting oligosaccharide to convert functional aldehyde groups into alcohol groups,
(c) fractioning the hydrogenated oligosaccharide according to molecular weight, so that the purified fraction has a weight average molecular weight equal to or less than 3,000 Daltons,
(d) combining the resultant fractionated hydrogenated oligosaccharide as an aqueous solution with at least one water-soluble ferric salt,
(e) adding base to the resulting aqueous solution to form ferric hydroxide, and
(f) heating the resultant basic solution to transform the ferric hydroxide into ferric oxyhydroxide in association with said oligosaccharide;

wherein step (c) comprises a procedure of purification by one or more membrane processes having a cut-off value between 340 and 800 Daltons, which procedure is continued until the content of dimer saccharide in the purified fraction of oligosaccharide has been reduced to 2.9% by weight or less, based on the total weight of the hydrogenated oligosaccharide. In principle, the purification could alternatively be done using other procedures for fractionation of oligosaccharides that are suitable for fractioning to a narrow range of molecular weights, e.g. chromatographic methods. However, purification by membrane processes is preferred. In any case, traditional fractionation technique based on precipitations is not a suitable fractionation technique for the present invention, as the oligosaccharide fraction obtained will be too diffuse.

Preferably, the initial hydrolysis of the polysaccharide is performed as an acid hydrolysis, using a strong mineral acid such as sulphuric acid, phosphoric acid or hydrochloric acid.

In a preferred embodiment, the hydrogenation of the resulting oligosaccharide is effected by addition of sodium borohydride in aqueous solution.

Preferentially, the obtained association of ferric oxyhydroxide with the oligosaccharide is stabilized by addition of at least one salt of an organic hydroxy acid, preferably selected from citrates.

Advantageously, said purification by one or more membrane processes having a cut-off value between 340 and 800 Daltons is continued until the content of monomer in the purified fraction of oligosaccharide has been reduced to 2.9% (w/w) or less.

The term polysaccharide is used in the present context to describe any polymer comprising monomer units of glucose. According to one embodiment, the applied polysaccharide is dextran.

The dextran is preferably purified in step (c) by one or more membrane processes having a cut-off value suitable for holding back dextran of molecular weight above 2,700 Daltons.

When adding base in step (e) to the resulting aqueous solution in order to form ferric hydroxide, said aqueous solution is preferably adjusted to a pH above 10.

The heating in step (f) favourably is carried out at a temperature above 100° C. until the solution turns into a black or dark brown colloidal solution, which after neutralisation is filtered, and one or more stabilizers are added. A useful filter is a 0.45 μm filter. Before addition of said stabilizers, the solution may also be subjected to further purification and stabilization using filtration, heating and membrane processes.

Finally, the resultant basic solution may in a preferred embodiment be dried to obtain the iron-dextran compound as a stable powder. Alternatively, the drying operation may be omitted, so that an injection liquid can be produced from the purified solution without intermediate drying thereof. The powder suitably contains an amount of iron (Fe) in the iron-dextran compound of 50% by weight or less.

According to an alternative embodiment, the polysaccharide employed is starch, or dextrin. Dextrins are usually made by depolymerisation of starch using known depolymerising means such as acids, bases or enzymes. Dependent on its origin, starch contains a certain amount of α 1,6-glucosidic bonds positioned at branch points of a polyglucose chain. Therefore, dextrins may also contain a similar low fraction of α 1,6-glucosidic bonds. By adjusting the conditions for the depolymerisation of the starch it may be possible to favour breakage of α 1,4-glucosidic bonds or α 1,6-glucosidic bonds, so that the ratio between these types of bonds differs between the original starch and the prepared dextrins.

One of the characteristic properties of starch and dextrin is their gelling properties. In contrast to dextran, starch and higher dextrins gels even at modest concentrations, which makes the handling more difficult.

The gelling tendencies of starch and dextrin are mitigated, when the molecular weight is reduced by hydrolysis. However, the hydrolysis should not be too extensive, as small dextrins, cf. above, may give rise to toxicity problems when combined with iron in an association complex. Preferably, starch is hydrolysed until it does not form strong coloured complexes with iodine. Solutions of starch hydrolysed to this extent comprise high amounts of dextrin in the desired molecular size range and present a viscosity that is sufficient low to allow easy and accurate handling. For hydrolysis of starch, hydrochloric acid is a preferred acid.

Before being combined with iron, the reducing capability of the dextrins is diminished. This may be done by hydrogenation of the terminal aldehyde groups of the dextrins to alcohols. This reduction may be performed using well known procedures. Hydrogenation using sodium borohydride is preferred. After the hydrogenation, the reducing capability of the dextrins should be less than 3.0% as determined by the cupric oxidation method.

In a preferred embodiment, dextrin in step (c) is purified to obtain a number average molecular weight (Mn) higher than or equal to 500 Daltons, wherein the 10% fraction of said hydrogenated dextrin having the highest molecular weight has a weight average molecular weight (Mw) of less than 4,500 Daltons, and 90% of the dextrins have a molecular weight of less than 3,500 Daltons.

In a particularly preferred embodiment the 10% fraction of the dextrins having the highest molecular weights has an average molecular weight less than 4,000 Da, 90% of the dextrins having molecular weights of less than 3,000 Daltons, and the 10% fraction having the lowest molecular weights has a weight average molecular weight of 800 Daltons or more. A dextrin of such a molecular weight distribution shows an appropriate viscosity and provides safe and stable association complexes with iron.

In step (d), the purified and hydrogenated dextrin as an aqueous solution is combined with at least one water-soluble ferric salt, a preferred example of which is ferrichloride.

In step (e), base is added to the resulting solution to form ferric hydroxide, preferably to obtain a pH above 8.5.

The resultant basic solution is heated in step (f) to transform the ferric hydroxide into ferric oxyhydroxide in association with the dextrin and preferably the heating is carried out at a temperature above 85° C. until the solution turns into a black or dark brown colloidal solution, which after neutralisation is filtered, and one or more stabilizers are added. Before addition of said stabilizers, the solution may also be subjected to further purification and stabilization using filtration, heating and membrane processes.

Finally, the resultant basic solution may in a preferred embodiment be dried to obtain the iron-dextrin compound as a stable powder. Alternatively, the drying operation may be omitted, so that an injection liquid can be produced from the purified solution without intermediate drying thereof.

According to a further aspect of the invention, the use of a compound according to the first aspect of the invention is provided for manufacture of a parenterally or orally administrable therapeutical composition for prophylaxis or treatment of iron-deficiency anaemia in animal or human subjects.

According to another aspect of the invention, a hydrogenated oligosaccharide is provided, having a weight average molecular weight (Mw) of less than 3,000 Daltons and a content of dimer saccharide of 2.9% by weight or less, and preferably a content of monomer of 0.5% by weight or less. Said oligosaccharide is an intermediate in the production of the iron oligosaccharide compound according to the first aspect of the invention.

According to an additional aspect of the invention, a process is provided for preparing said intermediate hydrogenated oligosaccharide according to the former aspect of the invention, which process comprises the steps of:
(a) hydrolysing a polysaccharide so as to reduce its molecular weight,
(b) hydrogenating the resulting oligosaccharide to convert functional aldehyde groups into alcohol groups, and
(c) fractioning the hydrogenated oligosaccharide according to molecular weight, so that the purified fraction has a weight average molecular weight equal to or less than 3,000 Daltons,
wherein step (c) comprises a procedure of purification by one or more membrane processes having a cut-off value between 340 and 800 Daltons, which procedure is continued until the content of dimer saccharide in the purified fraction of oligosaccharide has been reduced to 2.9% by weight or less, based on the total weight of the hydrogenated oligosaccharide. Preferably, said purification is continued until the content of monomer in the purified fraction of oligosaccharide has been reduced to 0.5% by weight or less.

According to a further aspect of the invention, a process is provided for producing an injection liquid containing a compound according to the first aspect of the invention, in which process the iron oligosaccharide compound as a dry powder is dissolved in an aqueous medium, pH is adjusted, if necessary, optionally stabilizer is added, and the liquid is sterilized by filtration, before it is filled into ampoules or vials, or by autoclave treatment after filling into such ampoules or vials.

Alternatively, a liquid containing said compound is purified, adjusted as to iron content and pH, stabilized and sterilized by filtration before being filled into ampoules or vials or by autoclave treatment after being filled into said ampoules or vials.

The iron oligosaccharide compounds according to the invention are highly soluble in water, which makes it possible to prepare injection liquids containing a high amount of iron. According to one embodiment of the invention, an injection liquid adapted for administration in a human is provided, comprising 1-20% (w/v) iron. Another embodiment of the invention provides an injection liquid adapted for administration in an animal comprising 10-30% (w/v) iron.

Solutions of the iron oligosaccharide compounds according to the invention can be sterilized by autoclaving without substantial physical changes of the solutions. Thus, the solutions may be autoclaved without any significant change of the molecular weights of the complexes or the viscosity of the solution.

The aqueous solutions of the iron oligosaccharide compound may be preserved using any recognized preserving techniques such as autoclaving, filtration through a 0.2-0.5 micron filter under sterile conditions or addition of a preserving agent. As an example of a preserving agent 0.5% phenol can be mentioned.

However, autoclaving is a preferred method for preserving the aqueous solutions of the compound according to the invention. Particularly preferred is autoclaving at a temperature of 121-135° C. for a period of 5-40 minutes.

The aqueous solutions of the iron oligosaccharide compound according to the invention show excellent stability and are not liable to deterioration by storage such as by gellification or precipitation.

The invention will now be further illustrated by the following non-limiting examples.

EXAMPLES

Hydrolysis and Hydrogenation of Dextran

An amount of pre-hydrolysed dextran collected as permeate from a membrane having a cut-off value<5,000 Daltons is further hydrolysed at pH 1.5 at a temperature of 95° C.

The hydrolysis is monitored using gel permeation chromatography (GPC) and is terminated by cooling, when the molecular weight of the material being hydrolysed is estimated to have achieved the desired value, i.e. a weight average molecular weight of 700-1,400 Daltons.

In the hydrolysis, low molecular weight dextran is produced but also glucose and iso-maltose are formed. Upon hydrolysis, the disaccharide content is at 7-8% by weight.

After cooling and neutralization, the amount of monomer and dimer is reduced by membrane processes having a cut-off value of 340-800 Daltons. The concentration of monosaccharide and disaccharide in the solution is monitored by gel permeation chromatography, and fractionation goes on until a dimer concentration of 2.9% by weight or less and a monomer concentration of 0.5% by weight or less is achieved.

Thereafter, the content of dextran is determined by optical rotation and the amount of reducing sugar is determined by use of Somogyi's reagent. To bring down the reducing capability below 3%, sodium borohydride is added to the solution at basic pH. The applied ratio of sodium borohydride:fractionated dextran is 1:34.7.

The solution is neutralized to pH<7.0 and subsequently de-ionized. The average molecular weights and the molecular weight distribution are determined chromatographically. Chromatography reveals that the desired conditions, viz. that 90% by weight of the dextran has a molecular weight less than 2,700 Daltons and that the weight average molecular weight (Mw) of the 10% by weight fraction of the dextran having the highest molecular weight is below 3,200 Daltons, are fulfilled. The final yield of dextran after de-ionization is approximately 50% relative to the initial amount of pre-hydrolysed dextran.

Synthesis of Iron-Dextran 120 kg dextran as produced above is mixed as an 18% solution with 150 kg $FeCl_3$, 6 $H_2O$. To the agitated mixture, 93 kg $Na_2CO_3$ as a saturated aqueous solution is added, whereupon the pH is raised to 10.5 using 24 liters of concentrated aqueous NaOH (27% (w/v)).

The mixture thus obtained is heated above 100° C. until it turns into a black or dark brown colloidal solution. After cooling, the solution is neutralized using 12 liters concentrated hydrochloric acid to obtain a pH of 5.8. After filtration the solution is purified using membrane processes until the chloride content in the solution is less than 0.55% calculated on basis of a solution containing 5% (w/v) iron.

If the chloride content of the solution is less than desired to obtain an isotonic solution, sodium chloride is added and pH is finally adjusted to 5.6, and the solution is filtered through a 0.45 μm (or alternatively a 0.2 μm) membrane filter.

The solution is spray dried and the iron-dextran powder is ready for marketing or for further processing.

As an alternative to spray drying, the solution may be used for direct production of injection liquids having an iron content of e.g. 10% (w/v), as described above.

When using the iron-dextran powder for producing injection or infusion liquids, the powder is re-dissolved in an aqueous medium, the pH is checked and, if necessary, adjusted, and the solution is filled into ampoules or vials after being sterilized by filtration. Alternatively, the sterilization can take place by autoclaving after filling into ampoules or vials.

Analysis of the Stability of Iron Oligosaccharide Compounds Relative to their Content of Dimer A range of iron oligosaccharide compounds with differing contents of disaccharide were analysed with respect to their rate of hydrolysis and apparent molecular weight, both of which are indicative of the quality of the respective compounds.

The rate of hydrolysis of $Fe^{3+}$ from the compound of FeOOH and oligosaccharide in acidic solution (0.24 M HCl; 0.9% NaCl) is assumed to be correlated to the rate of physiological release of iron. Therefore, the rate of hydrolysis as expressed by the half-life ($t_{1/2}$) is an important parameter of the investigated compounds.

The hydrolysis of $Fe^{3+}$ was measured by optical absorbance at 287.3 nm.

Besides, it was found that the thermostability of iron oligosaccharides is a function of their apparent molecular weight ($M_P$). Thus, such compounds are unstable to an unsatisfactory degree, if the apparent molecular weight markedly exceeds a value of 160,000 Daltons upon storage at an elevated temperature for three months as test solutions.

The results are shown in Table 1.

TABLE 1

| Iron oligosaccharide compound no. | Amount of dimer in oligosaccharide | $t_{1/2}$/hours | $M_P$/Daltons | Assessment after keeping at elevated temperature for 3 months |
|---|---|---|---|---|
| 1 | 0.5% | 25.5 | 133,490 | stable |
| 2 | 0.75% | 21.7 | 149,532 | stable |
| 3 | 0.75% | 22.5 | 146,353 | stable |
| 4 | 1.6% | 21.6 | 138,053 | stable |
| 6 | 1.6% | 18.3 | 145,250 | stable |
| 7 | 2.0% | 20.9 | 150,983 | stable |
| 8 | 2.0% | 20.3 | 142,664 | stable |
| 9 | 3.0% | 12.1 | 152,516 | unstable |
| 10 | 5.0% | 12.2 | 185,433 | unstable |
| 11 | 8.0% | 9.7 | 215,143 | unstable |

As appears from Table 1, the apparent molecular weight is in a desirable range, viz. about 130 kD to about 160 kD, when the amount of dimer in the oligosaccharide is less than 3%. The same holds true for the rate of hydrolysis as expressed by the half-life. The Half-life ($t_{1/2}$) is defined as the time at which the absorbance is the half of the value compared the absorbance at t=0.

The results shown in Table 1 above may be arranged into two series. When the results are plotted into a diagram of $t_{1/2}$ vs. the dimer content FIG. 1 appears. The two straight lines fitted into the two series show an interception at a dimer content of 3.5% by weight and $t_{1/2}$ of 12.6 hours.

The invention claimed is:

1. A process for preparing a hydrogenated oligosaccharide, which process comprises the steps of:
   (a) hydrolysing a polysaccharide so as to reduce its molecular weight,
   (b) hydrogenating the resulting oligosaccharide to convert functional aldehyde groups into alcohol groups, and
   (c) fractioning the hydrogenated oligosaccharide according to molecular weight, so that the purified fraction has a weight average molecular weight between 500 and 3,000 Daltons,
   wherein step (c) comprises a procedure of purification by one or more membrane processes having a cut-off value between 340 and 800 Daltons, which procedure is continued until the content of dimer saccharide in the purified fraction of oligosaccharide has been reduced to 2.9% by weight or less, based on the total weight of the hydrogenated oligosaccharide,
   wherein the hydrogenated oligosaccharide is hydrogenated dextran oligosaccharide having a number average molecular weight (Mn) above 500 Daltons, 90% by weight of said dextran has molecular weights less than 3,500 Daltons, and the weight average molecular weight (Mw) of the 10% by weight fraction of the dextran having the highest molecular weights is below 4,500 Daltons, and wherein the Mw is between 850 and 1150 Daltons.

2. The process according to claim 1, wherein said purification is continued until the monomer saccharide content in the purified fraction of oligosaccharide has been reduced to 0.5% by weight or less, based on the total weight of the hydrogenated oligosaccharide.

* * * * *